United States Patent [19]

Cook

[11] Patent Number: 5,945,171
[45] Date of Patent: Aug. 31, 1999

[54] AQUATIC ORGANISM AND CORROSION RESISTANT COATING AND METHOD FOR PRODUCING THE COATING

[75] Inventor: Leon Edmond Cook, Montgomery, Ohio

[73] Assignees: Ryan A. Cook, Ferndale, Mich.; Shannyn M. Cook, Cincinnati, Ohio; heirs of deceased

[21] Appl. No.: 08/954,429

[22] Filed: Oct. 20, 1997

[51] Int. Cl.[6] .............................. B05D 1/10; A01N 59/20
[52] U.S. Cl. ...................... 427/456; 106/15.05; 424/630; 424/646; 427/448; 427/449; 427/455
[58] Field of Search ...................... 106/15.05; 424/78.09, 424/630, 646; 427/448, 449, 455, 456

[56] References Cited

U.S. PATENT DOCUMENTS

| | | | |
|---|---|---|---|
| 4,526,839 | 7/1985 | Herman et al. | 428/550 |
| 4,814,227 | 3/1989 | Maeda et al. | 428/353 |
| 5,164,157 | 11/1992 | Clark et al. | 420/486 |
| 5,253,954 | 10/1993 | Landsberger | 405/122 |
| 5,266,105 | 11/1993 | Tsuneta et al. | 106/16 |
| 5,284,682 | 2/1994 | Martin | 427/386 |
| 5,304,236 | 4/1994 | Fears | 106/15.05 |
| 5,358,749 | 10/1994 | Fears | 106/15.05 |
| 5,441,554 | 8/1995 | Romero et al. | 75/255 |

OTHER PUBLICATIONS

David B. Harwood and Dennis J. Buda, "Detroit Edison Conquers Zebra Mussels", Power Engineering Magazine, Nov. 1993.
Roy I. Marcus and Steven L. Wahlert, Thermal Treatment Effectively Controls Zebra Mussels at Illinois Power Plants, Power Engineering Magazine, Dec. 1994.
Computer Search Results of Patent database on Key Words Biofouling and Control Feb. 18, 1997.
Computer Search Results of Patent Database on Key Words Zebra and Mussel Feb. 18, 1997.
Sea Grant Minnesota, "Zebra Mussels Threaten Inland Waters" Aug. 29, 1996.
U.S. Geological Survey, "Zebra Mussel Distribution Update" Jul. 1997.
U.S. Geological Survey, "Map of Zebra Mussel Distribution" Jul. 1997.
U.S. Army Corps of Engineers, "Coating to Repel Zebra Mussels", Apr. 1997.
Richard C. Maxson "Evaluation of Zebra Mussel Resistant Materials of Contruction for Intake Screens and Assemblies" Mar. 9, 1994, Poster Session 4th International Zebra Mussel Conference.
Chemical Abstract No. 124:241386 which is an abstract of an article by Dormon et al entitled "Copper and copper--nickel alloys as zebra mussel antifoulants", J. Environ. Eng. 122 (4), 1996.

*Primary Examiner*—Anthony Green
*Attorney, Agent, or Firm*—Flynn, Thiel, Boutell & Tanis, P.C.

[57] ABSTRACT

This invention consists of a coating that is zebra mussel resistant and biofouling resistant without dependence on copper leaching. The coating is a solid solution of copper and nickel containing at least 65 percent copper. Application of the coating to stationary screens, traveling water screens, trash racks, louvers, and other components of water withdrawal and hydroelectric systems, netting and other porous materials used in barrier nets, fish nets, aquaculture, and fish hatcheries, the bottoms of water craft including recreational craft, boats, and ships and on bouys, piers and pilings and other materials that might benefit from resistance to the attachment of zebra mussels and other aquatic or marine organisms. Unlike coatings that depend on release of copper or copper ion for resistance, the rate of copper and copper ion release into the surrounding waters when measured using NSF International standard leach testing protocol and USEPA certified testing procedures is below the practicable detection limits of the equipment of 50 parts per billion.

13 Claims, No Drawings

AQUATIC ORGANISM AND CORROSION RESISTANT COATING AND METHOD FOR PRODUCING THE COATING

FIELD OF INVENTION

The invention generally pertains to coatings, and more specifically, coatings that are resistant to zebra mussels attachment and biofouling attachment.

BACKGROUND AND DESCRIPTION OF RELATED ART

Zebra mussels were first reported in U.S. waters in the mid to late 1980's. The mussels live in fresh water and are not native to North America. Initially they were identified in Lake Erie and there was much discussion of the possibility that they would not live in the other Great Lakes, nor would they survive in inland rivers, lakes, ponds, or streams. Viable populations of the mussels have since been found throughout the Great Lakes, as far north as the upper reaches of the St. Lawrence Seaway and the Mississippi River past Minneapolis, Minn. They are present in the Illinois River, the Hudson River, and the St. Croix River. They have been found as far south in the Mississippi River as Vicksburg, Miss. and are present in the Atchafalaya River Basin. They have been found in the Arkansas River, the Tennessee River, the Ohio River from Cairo, Ill. to its confluence with the Monongahela at Pittsburgh, Pa. and in the Monongahela near Monesson, Pa. They have also been found in 45 inland lakes in Michigan, 15 lakes each in Indiana and New York, 8 inland lakes in Ohio and 7 inland lakes in Wisconsin. They have also been found in Lake Champlain in Vermont and Lakes Saratoga and George in New York.

The spread of zebra mussels may be due, in part, to its reproductive cycle. It is reported that a fully mature female mussel may produce several hundred thousand eggs per reproductive season. The eggs are fertilized outside the mussels body and within a few days develop into free swimming larvae called veligers. The veligers grow into the typical double shelled mussel shape. Within a year, a zebra mussel can grow up to an inch and become sexually mature. The mussels can become established regardless of depth, light intensity or winter temperature. Colonies of the mussels seem to grow rapidly wherever oxygen and particulate food is available and where the water currents are generally less than 6 feet per second. The mussels have also been found to colonize soft, sandy or muddy bottoms. Extensive mats of mussels several inches thick have been found on lake bottoms and on the inside and outside of pipes.

The attachment and growth of zebra mussels on water intake screens, intake structures, intake pipelines, boat bottoms, fisherman's nets, fish barrier nets, and virtually any other surface in the infested waters is a significant problem in the fresh waters of the United States.

Similarly, biofouling, the attachment and growth of aquatic organisms on submerged surfaces in fresh water, sea water, and all the intermediate water mixtures can interfere with the water supply, increase energy and fuel use requirements, increase corrosion rates, and generally cause problems and increase maintenance requirements.

For years it has been recognized that, at many locations, when pure copper or alloys high in copper content were used in sea water or mixtures of sea water and fresh water, the attachment and growth of aquatic organisms on the material was much less severe than on other materials. At a minimum, the strength of the attachment bond of the organisms to the material was not as strong to the copper based materials as it was to other materials—making cleaning and removal of the organisms easier. In general, biofouling in fresh waters was not a major concern because the fresh water organisms didn't create major problems.

The mechanism by which these alloys afford resistance to the attachment and growth of organisms in the water has generally been believed to be as a result of the release of copper or copper ions into the water source. It is commonly suggested that the biofouling resistance of copper and copper alloys is the result of copper dissolving into the water and "poisoning" the organisms. It has been observed that when some corrosion products form on the surface or debris accumulates on the surface, organisms attach to the debris or to the portion of the surface with corrosion products.

Zebra mussel attachment resistance and resistance to biofouling organism attachment without dependence on copper leaching is the unique combination of characteristics of copper nickel materials. Copper and nickel form a solid solution throughout all combinations of concentrations from 100% copper and 0% nickel to 0% copper and 100% nickel. The characteristic resistance to corrosion in fresh and sea water of the individual elements seems to be enhanced when the two elements are combined in solid solution. When the copper concentration in the solid solution equals or exceeds 65% resistance to the attachment of marine organisms has been observed. When the concentration of copper in the solid solution is in the range of 90% resistance to the attachment of zebra mussels is observed. The precise mechanisms for this resistance to attachment is not known. It may be as a result of increases in the thermal or electrical conductivity of the material which increases with increasing copper concentration. It may be as a result of the surface energy of the material. It may be as a result of the formation of oxides of copper and nickel which form on the material surface. The great resistance to corrosion of the copper nickel solid solutions in fresh and sea waters is a strong indicator that the mechanism of resistance to organism attachment is not a result of copper or copper ion leaching into the water.

The arrival of zebra mussels in U.S. waters created a new and significant biofouling problem in our fresh waters. The mussels' behavior of growing rapidly, attaching and growing on virtually any object, and growing on other mussel shells has resulted in clogging of water intake pipes and trash racks; interference with the operation of locks and dams; fouling of boat bottoms, fish nets, and barrier nets; and build ups that weigh down bouys, reducing their visibility and effectiveness.

An array of control and management techniques have been applied to biofouling and zebra mussel control.

One technique is chemical control. This is particularly common on intake systems and intake pipelines. Chlorine, chlorine dioxide, potassium permanganate or other disinfection chemicals are introduced into the water to kill the zebra mussels and their larvae. Chemical control can be effective. Chemical control also has problems. It can be expensive to install and operate a chemical control system. Great care must be used in handling the chemicals as they can be toxic to humans, as well as desirable aquatic organisms such as fish. Care must be exercised in the dispersal of the chemicals. Release of the chemicals into the open water source could result in death to fish and other desirable creatures in the water. Management and control of the chemicals can also be a hazard to people using the water that has been treated. The natural action of the chemicals produces disinfectant by-products which can be dangerous, particularly in drinking water supplies.

A second technique is the use of very warm water. Subjecting zebra mussels to very warm water has been found to kill the mussels or inhibit their growth or reproductive systems. The use of heat can be effective. The use of heat also has its problems. Among these problems are the need for a source of a significant quantity of very warm water. A thermal electric generating station may have a source for such water, a municipal treatment plant might find the production of a sufficient quantity of very warm water excessively expensive. If a sufficient quantity of very warm water is available then the next problem with this technique must be addressed—getting the water to the point where control is desired. This can often be very expensive and difficult to accomplish. The use of very warm water for control also presents challenges with regard to environmental protection. Introduction of very warm water into the source water body can distort the natural ecosystem in the vicinity of the heated water discharge. Sudden loss of supply of the very warm water can result in thermal shock that kills fish that have been attracted to the area. The need for control of the zebra mussels must be balanced against the possible damage to fish and other aquatic organisms in the water body and the cost of producing and delivering the water.

A third technique is the use of pure copper as the material of construction. It has been reported that a copper alloy with copper concentration of 70% produced no noticeable reduction in zebra mussel attachment when compared to stainless steel or acrylic material. There are reports of copper alloy materials producing successful resistance to zebra mussel attachment and growth. The composition of the materials is not identified in the reports. Construction with materials containing high concentrations of copper, 70% or more in sea water and higher for zebra mussel control, may be an effective control technique. Construction with materials containing 70% or more copper also has problems. In general, these alloys are soft and not very strong. As a result, more material is required to provide the structural integrity required by the application. The materials are heavy—about 10% heavier than steel or stainless steel. When weight and strength are both design factors, the copper and copper alloy materials may require 50% to 100% greater weight of material than a similar construction in stainless steel. The materials are expensive, costing 2½ to 5 times as much as stainless steel. The materials, particularly the alloys, are not always readily available in the required shapes, sizes or thicknesses to allow their use in construction. Copper and some of the alloys corrode readily in fresh water, sea water, and mixtures. As a result, these materials also have a limited service life—they waste away. They release copper and copper ion into the water. There are also some indications that the presence of corrosion products on the material surface interferes with their biofouling and zebra mussel resistance. Corrosion of the material creates an additional problem for municipal water systems. These systems must meet a lead-copper concentration standard at the water taps of their customers. Corrosion of copper materials in these systems could make meeting the standard more difficult.

A fourth technique is mechanical cleaning. Zebra mussels and other biofouling organisms can be removed by scraping, chipping, plucking, or blasting the material off the surface to be cleaned. Divers may work under water to remove the unwanted organisms or the surface of interest can be removed from the water, the organisms removed, and then the surfaces returned to the water. This technique can be effective but it also has its problems. The principal problems are cost and accessibility. In some cases it is very difficult for divers to be able to reach and clean the surfaces that need to be cleaned.

The fifth technique is the use of coatings. The coatings are of generally two forms: One form is copper-containing paints and organotin paints that have been used to control fouling on boat bottoms for years. A variety of antifouling paints have been developed for sea water applications and are currently being employed for zebra mussel resistance. This form of coating is designed to inhibit the attachment and growth of organisms on the coated surface through the release of material toxic to the organisms of concern. The second form is coatings that depend on slipperiness to minimize the strength of attachment of zebra mussels and biofouling. These coatings don't resist attachment, instead they are intended to make removal of the attached growth easier or depend on high local velocities to remove accumulated materials. Some work has been done on cladding of surfaces for control of marine biofouling. Thin layers of copper or copper alloy sheet are secured to the structure to be protected. Coating with copper bearing paints, organotin paints, antifouling paints, and cladding can be effective. These coatings also have problems. Paints tend to lose their biofouling resistance over time as the toxic components are lost and the paints need to be reapplied on a regular basis. In fact, the preponderance of these paints that have been demonstrated to be effective are "ablative" by design. The paints are designed to wear away so that new biofouling or zebra mussel resistant material is exposed. There are also problems with the binders used in the paint and difficulties with wear and abrasion of the coatings when the materials are placed in natural waters. These coatings are designed to have a relatively short term service life and intended to be re-applied on a regular basis to maintain resistance to attachment and growth. For both the coatings intended to provide resistance and the coatings intended to enhance the slipperiness of the surface, there are problems with the carriers used in the paints. The carriers are often volatile organic compounds and the application process must be done in such a way as to minimize the release of these VOC's to the surrounding environment. An additional problem with all of the paints is application—particularly to structures such as water intake screens with smaller openings. The paint has a tendency to block the openings in the screen and preclude water from entering the system. A further problem with many forms of coatings and cladding is that they are frequently thick and not particularly flexible. As a result, application of the coating on items such as fish nets makes it impossible for them to be used for their intended purpose.

Claddings are generally expensive, difficult to install, and, in some cases, impossible to install in such a way as to provide the desired coverage and protection.

SUMMARY OF INVENTION

To avoid the limitations and problems with present zebra mussel and biofouling control techniques, an objective of this invention is to provide a coating that is zebra mussel resistant and biofouling resistant without depending on copper leaching. Another objective of the invention is to produce such a coating on surfaces that are adversely impacted by the attachment of zebra mussels or other biofouling organisms. Another objective of the invention is to produce such a coating that does not depend on release of copper or copper ion to accomplish resistance to organism attachment. Another objective of the invention is to produce such a coating on the surfaces of equipment such as stationary water intake screens, mechanical water intake screens, trash racks, trash rakes, louvers, and other components of water withdrawal and hydroelectric generating systems.

Another objective of the invention is a method to produce such a coating on netting and other barrier or collection materials used for fish pens, barrier nets, and porous separation devices such as those used in fish hatcheries and aquaculture farms. Another objective of the invention is to produce such a coating on the bottoms of water craft including recreation craft, boats, and ships and on navigational devices and aids such a bouys. These and other objects of the invention are provided by the use of a material that is a solid solution of copper and nickel, with more than 70% copper. Unlike coatings based on toxic release, the use of this material selection produces a coating that provides resistance to zebra mussel and other biofouling attachment on the coated surface, is corrosion resistant, and, as confirmed by testing performed in conjunction with development of the coating, this resistance to zebra mussel and biolouling organism attachment is accomplished without measurable release of copper or copper ion as measured using standard NSF International leaching measurement protocals and USEPA certified detection techniques capable of detection to 50 parts per billion. As a result, protection from biological attachment and growth is accomplished, long service life is provided, and both are achieved without depending on copper or copper ion leaching from the coating.

DESCRIPTION OF PREFERRED EMBODIMENT

The reason for the inventive coating that is zebra mussel resistant and biofouling resistant without dependence on copper leaching is that the desireable characteristics of the copper nickel solid solution are retained through the coating application process. The combination of coating production method and materials selected for application may also enhance the formation of oxides on the coating that further minimize the rate of material loss from the coating. In the inventive method, wire of a nominal composition of 90% copper and 10% nickel can be used. Coating using this material and applied using the method discussed herein produces a coating that is resistant to the attachment of zebra mussels. The coating is also corrosion resistant and resistant to the attachment of biofouling organisms. The wire is mounted in a thermal spray device. In the arc spray variation of thermal spraying, a twin wire feeder pushes two wires through the arc spray gun. The high heat zone created by the arc generated between the two wires melts the wires and compressed air blows the molten particles onto the surface to be coated.

The coating is applied to the surface by directing the spray of particles at the surface to be coated and moving the gun across the surface while the spray is directed at the substrate surface. The thickness of the coating is controlled by the speed of material delivery through the gun, the speed of gas flow through the gun, the distance from the gun to the target substrate, the angle between the spray direction and the substrate, and the speed of gun movement over the substrate surface.

The distance from the arc spray gun needs to be controlled so that the distance from the gun to the target substrate is large enough to minimize the amount of coating material that is blown off the substrate by the compressed air or compressed gas. The distance from the arc spray gun needs to be controlled so that the distance from the gun to the target substrate is small enough to minimize the amount of coating material that fails to reach the substrate or fails to adhere or bond to the substrate. Precise control of the distance from the gun to the substrate does not seem to be a critical factor. A distance from the gun to the substrate of about 3" as been found to be effective.

The angle of the spray from the gun to the substrate does not seem to be critical. In the direction of gun travel, an angle of 90 degrees has been found to be effective. Shallower angles of the gun to the substrate have also been found to be effective. Very shallow angles can be used. It does seem to be important that there be a direct path between the tip of the gun and the substrate surface to be coated. The angle of the spray to the substrate perpendicular to the direction of gun travel does not seem to be critical. An angle of 90 degrees has been found to be effective. Shallower angles of the gun to the substrate have also been found to be effective. Very shallow angles can be used. It does seem to be important that there be a direct path between the tip of the gun and the substrate surface to be coated. When angles other than 90 degrees are used it does not seem to be significant whether the spray from the gun is into the direction of travel or backward along the direction of travel.

A variation of the composition of the coating employing a material of a composition of 65 percent or more copper and the principal secondary element being nickel can also be employed. The composition of the coating can be controlled either through the composition of the material used for the coating or control of the mixtures of materials being used to create the desired composition.

A variation in the thermal arc spraying involves the use of an inert gas to blow the produced particles onto the surface to be coated and to provide a protective shield around the molten particles as they are being projected onto the surface.

Another variation in the thermal arc spraying is to use duplex wires made up of copper and nickel. A copper core wrapped with a nickel overwrap or a nickel core wrapped with a copper overwrap can be used. In this variation, the copper-nickel solid solution coating is actually created during the process of the melting of the wire in the high heat zone created by the arc generated between the two wires.

Another variation of the thermal spray technique is thermal plasma spraying. In this variation, a hot ionized gas is used to melt a powder and propel it onto the substrate through the expanding plasma gas. The powder can consist of either a material made up of the desired solid solution of copper and nickel or a mixture of copper and nickel powders of the desired composition and the solid solution would be formed during the melting process.

Another variation of the coating application technique is intermittent coating. In this variation, the material application rate or the angle of application or the distance between the gun and the surface to be coated are adjusted to produce an intermittent coating where the distance between adjacent applied coating particles is relatively small. If intermittent coating is selected for the substrate, protection is afforded only on those portions of the surface that are coated. Continuous coating would provide complete protection. Intermittent coating would provide less protection.

On metal surfaces, it is anticipated that appropriate preparation of the surface to be coated will be required. There may be particular applications and materials to be coated where surface preparation is not required. A number of surface preparation techniques may prove effective. Standard abrasive blasting of the surface with silica sand, alumina, or silicon carbide abrasive in the 40 to 120 grit size range has proven to be an effective surface preparation technique.

Through the use of thermal spraying of a copper-nickel mixture containing at least 65% copper, a bio-fouling and corrosion-resistant coating can be easily and economically applied to an object that is to be exposed to a marine environment. The type of object is not limited and can be any object that can be thermal spray coated.

What is claimed is:

1. In a method of preventing the fouling of a surface of an object by an aquatic organism, the improvement comprising the steps of thermal spraying a copper-nickel mixture containing at least 65% copper onto the surface of the object and forming a coating containing a copper-nickel solid solution on the surface of the object.

2. The method of claim 1, wherein said object is a stationary intake screen.

3. The method of claim 1, wherein said object is a debris barrier.

4. The method of claim 1, wherein said object is a navigational aid.

5. The method of claim 1, wherein said object is a water craft.

6. The method of claim 1, wherein said object is a mechanical water screening device.

7. The method of claim 1, wherein said object is a net.

8. The method of claim 1, wherein said object is a pier or a piling.

9. The method of claim 1, wherein said copper-nickel mixture contains at least 85% copper.

10. The method of claim 9, wherein said aquatic organism is a zebra mussel.

11. The method of claim 1, wherein the thermal spraying is performed by a twin wire thermal arc spray gun and compressed air is utilized to blow molten droplets of the copper-nickel mixture onto the surface of the object.

12. The method of claim 1, wherein said coating is formed by thermal plasma spraying and compressed air is utilized to blow molten droplets of the copper-nickel mixture onto the surface of the object.

13. The method of claim 1, wherein said coating is formed by thermal plasma spraying and an inert gas is utilized to blow molten droplets of the copper-nickel mixture onto the surface of the object.

* * * * *